US006192702B1

(12) United States Patent
Shimogori

(10) Patent No.: US 6,192,702 B1
(45) Date of Patent: Feb. 27, 2001

(54) PERSONAL COOLING DEVICE

(76) Inventor: Kotaro Shimogori, 600 Flower Ave. #3, Venice, CA (US) 90291

( * ) Notice: Subject to any disclaimer, the term of this patent is extended or adjusted under 35 U.S.C. 154(b) by 0 days.

(21) Appl. No.: 09/286,172

(22) Filed: Apr. 5, 1999

(51) Int. Cl.[7] .................................................. F25D 23/12
(52) U.S. Cl. ............................................ 62/259.3; 62/406
(58) Field of Search ................................... 62/259.3, 406, 62/457.2, 420

(56) References Cited

U.S. PATENT DOCUMENTS

| 4,612,774 | 9/1986 | Budreau | 62/59 |
|---|---|---|---|
| 4,751,827 | 6/1988 | Villarreal | 62/406 |
| 4,860,556 | 8/1989 | Hammett | 62/406 |
| 5,046,329 | * 9/1991 | Travis | 62/259.3 |
| 5,062,281 | * 11/1991 | Oliphant et al. | 62/406 X |
| 5,197,301 | 3/1993 | Holcomb | 62/457.1 |
| 5,953,933 | * 9/1999 | Cheng | 62/420 X |

* cited by examiner

Primary Examiner—Corrine McDermott
Assistant Examiner—Chen-Wen Jiang
(74) Attorney, Agent, or Firm—Cislo & Thomas LLP

(57) ABSTRACT

A PERSONAL COOLING DEVICE that may be slung about the neck of a wearer for providing personal cooling under various conditions and wherein the device may be stowed about the waistband of a garment of the user of the device when not used for cooling purposes.

9 Claims, 1 Drawing Sheet

PERSONAL COOLING DEVICE

SUMMARY OF THE INVENTION

A personal cooling device taking the form of a lightweight, low-cost manufactured personal air conditioner which is battery powered and which may utilize one of a plurality of cooling packs, but the preferred one is a gel pack that is easily installed and which provides cooling for the user under hot weather conditions, as may be found in outside amusement parks and the like.

BACKGROUND OF THE INVENTION

1. Field of the Invention

With the popularity of amusement parks like those found in warm climates such as Disneyland, Knott's Berry Farm and the like, it has been necessary to locate these amusements centers in areas where land values are moderately priced, but which have the deficit of being uncomfortable in a climatic sense during hot spells especially during summer months.

It is not unusual in these amusements parks, during the height of the tourist season as encountered in summer months, to have temperatures in the 90° plus area. Being able to have a personal, lightweight cooling device such as a portable fan which emits cool air to which the invention is directed is a decided plus for any attendee at for example, amusement parks during uncomfortable warm weather conditions.

2. Description of the Related Art

As far as known, the prior art has attempted to provide various ingenious means of having cool air with just the utilization of a fan, but none have come up with the idea of a personal air conditioning type of device which is easily manufactured, relatively low-cost and simple in operation.

The patents in the prior art of which the inventor is aware are as follows:

Ice Cooled Screen Apparatus and Method, U.S. Pat. No. 4,612,774

This patent relates to an apparatus and method for providing an ice cooled fan screen wherein a support frame is designed as a chamber suitable for holding ice and wherein the device is intended to be placed in front of a fan such that the movement of air through the ice cooled fan screen provides the cooling effect.

Air Cooling and Directing Apparatus, U.S. Pat. No. 4,860,556

This patent relates to a plastic container of the type to confine a freezable liquid much like that found in conventional gel packs, wherein the container is mountable over the protective enclosure of a multi-bladed air moving fan such that air driven by the fan passes through the channels of the container to thereby provide cool air.

Fan Air Cooler, U.S. Pat. No. 4,751,827

This patent relates to a fan air cooler for attachment to a conventional electric fan and has a grid of spaced strips filled with a frozen fluid material. The strips have spaced fluid sacks which resemble ice cubes and the attachment is secured to a fan housing by magnets, adhesive or VELCRO such that the air passing through the attachment is cooled.

Ice Cooled Air Conditioner and Method, U.S. Pat. No. 5,197,301

This patent discloses a battery operated fan device which may be used in environments such as camping tents and similar such locations where high voltage of electrical power is not available and wherein the battery operated fans are positioned to direct air through conduits or ducts, which allow for the passage of the air, in a heat exchange relationship, through frozen material such as ice to thereby provide cool air.

DISCLOSURE OF THE INVENTION

The invention is directed to a personal cooling device comprising the combination of a body member forming an open-top housing containing a switch actuated, motor operated fan adapted to be battery energized and having a platform positioned over the fan blade, which platform is adapted to receive a coolant member such as a gel pack with a screw-type cap member being releasably secured to the open top housing to provide ease of access into the housing in order to replace the gel pack after the same has been used up with respect to providing cooling.

In its most specific form, the invention is directed to a personal cooling device comprising the combination of a body member having an upper, wide-mouth portion forming a recess and a lower conically shaped portion, the upper wide-mouth portion having a retaining means within the recess and being adapted to retain a coolant member, such as a gel pack, in releasable fashion thereon. A fan blade is operatively disposed within the recess and below the retaining means and the housing wall contiguous to the fan blade has spaced apertures communicating to the ambient atmosphere, while the lower conically shaped portion houses a motor operatively connected to the fan blade and being adapted to receive batteries in energizing relationship to the motor. Switch and circuit means for energizing the motor and a cap member releasably associated with the wide mouth portion of the body member completes the device. The device also has a clip provision whereby the same may be clipped onto the waistband of a wearer, when not being directly utilized to cool the face of the wearer and to provide that accomplishment, a means of attaching a tether on lanyard to the device is employed so that the cooling device may be hung around the neck of a wearer.

OBJECTS OF THE INVENTION

It is an object of the invention to provide a personal cooling device of lightweight, essentially maintenance-free operation which may be hung around the neck of a wearer for personal cooling.

It is another important object of the invention to provide a personal cooling device which forms a container which is easily accessible and which is adapted to hold a coolant such as a gel pack.

It is another important specific object of the invention to provide a personal cooling device which may be utilized in amusement park environs such that a battery operated fan provides, in conjunction with a gel pack coolant, a supply of cool air for as long as two hours.

It is another important specific object of the invention to provide a personal cooling device which is easily carried on the waistband of a garment of the wearer and wherein in an alternative mode, the device may be worn around the neck in order to provide cooling air.

It is another even more specific important object of the invention to provide a personal cooling device that is capable of giving cooling and soothing air in an otherwise heated and uncomfortable environment.

These and other objects of the invention will become apparent from the hereinafter following commentary taken in conjunction with the drawings.

DESCRIPTION OF THE PREFERRED EMBODIMENT(S)

Figure 1:
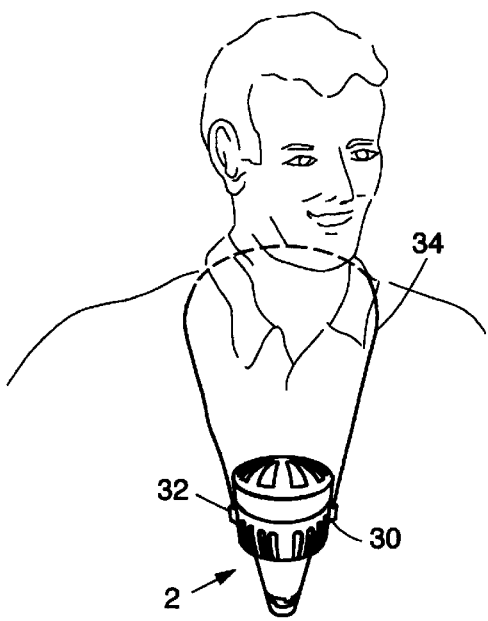
FIG. 1 is a perspective view showing how the invention may be utilized about the neck of a wearer.
Figure 2:
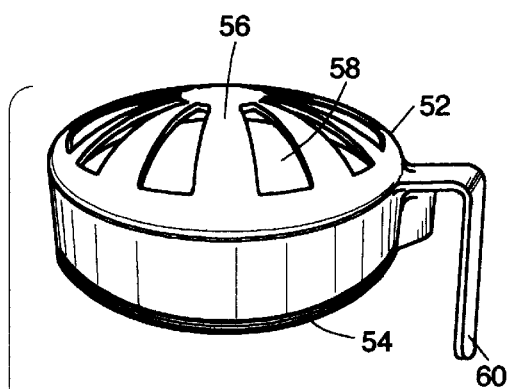
FIG. 2 is an exploded view of the PERSONAL COOLING DEVICE illustrated in FIG. 1.
Figure 2:
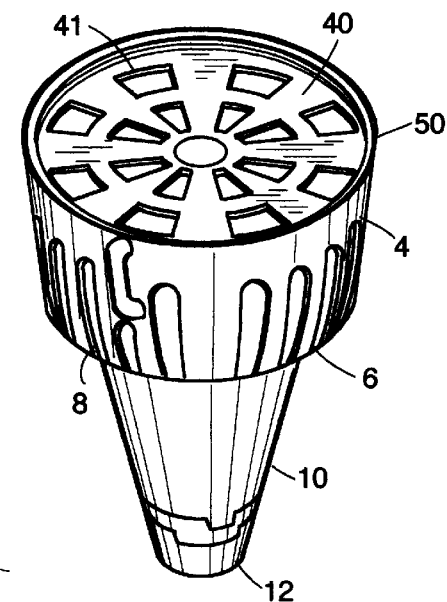
Figure 3:
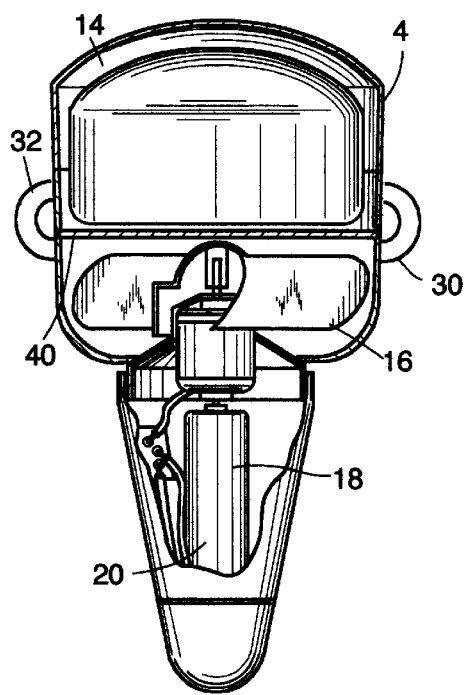
FIG. 3 is an enlarged schematic illustration showing some of the main components of the PERSONAL COOLING DEVICE of the invention.

The detailed description set forth below in connection with the appended drawings is intended as a description of presently preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequence may be accomplished by different embodiments that are also intended to be encompassed within the spirit and scope of the invention and the claims thereon.

Referring to the drawings wherein like numerals of reference designate like elements throughout, it will be seen that the PERSONAL COOLING DEVICE of the invention 2 comprises a main circular body member 4 of open top configuration having larger diameter wall portion 6 with spaced apertures 8 and in this particular instance being of unitary construction and having a lower conically shaped wall portion 10 with its terminus 12 comprising a rotating switch element for purposes that will become apparent.

The main circular body member portion 4 forms an interior recess 14 within which is disposed, in operable fashion, fan blade 16 powered by motor 18 which is energized, in this particular instance, by a single double "A" battery 20.

In opposed relationship on the wall 4 are two opposed integral loops 30 and 32 by which a lanyard or tether 34 may be secured such that the PERSONAL COOLING DEVICE 2 may be hung around the neck of a person as seen in FIG. 1.

Secured within the recess 14 in superposition to the fan blade 16 is apertured retaining means 40, having spaced apertures 41 and forming a platform to support a coolant such as for example, a gel pack 42 having a maximum diameter and height to fit within the recess 14 and upon the retaining means 40. Obviously an ice pack or similar alternative may be used.

The upper rim of housing member 4 as at 50 may have screw threads thereon by which to retain cap member 52 which has corresponding threads 54 by which the cap 52 is easily secured to housing member 4 by simple screw or twist action. The cap 52 forms a dome shaped interior so as to accommodate the gel pack 42. The upper wall 56 of cap 52 has spaced apertures 58 for purposes to be described. The cap 52, in this particular instance, is provided with a lower, depending clip-like member 60 which is adapted to be hung or placed upon the waistband of a garment of a wearer when the PERSONAL COOLING DEVICE 2 is not in use as in the neck hung position as shown in FIG. 1. That is, for example, where the PERSONAL COOLING DEVICE 2 is used in amusement park environs when one no longer wishes to have the cooling effect or wishes to go on a roller coaster, one merely takes the neck slung PERSONAL COOLING DEVICE 2 off of from around his or her neck and clips the device onto the waistband of his or her trousers, for example.

In the assembled form, as seen in FIG. 1, the PERSONAL COOLING DEVICE 2 with the frozen gel pack 42, in position, is placed around the neck of the user as shown in FIG. 1 and the lower switch 12 turned on to energize the motor 18 to thereby cause fan blade 16 to rotate. The rotation of the fan blade 16 with its conventional configuration draws ambient air through the apertures 8 of body member 4 to thereby flow air through the retainer 40, and more specifically the spaced apertures 41 to contact the exterior surfaces of gel pack 42 to become cooled and thereafter be expelled through the apertures 58 of cap 52 in the general direction of the neck and face and head of the user, as shown in FIG. 1, to thereby provide a cooling effect.

In other instances, a wire stand, not shown, may be used to hold the PERSONAL COOLING DEVICE 2 in a secure and stable position so, upon activation, cooling air is provided, as for example, in an enclosed tent, in a non-air conditioned automobile, or some other such locale, including a dwelling, office, etc. where conventional air conditioning is not available.

Thus, a PERSONAL COOLING DEVICE has been disclosed which is of relatively low cost to manufacture, simple to operate and relatively trouble-free in operation.

In utilization of the device, one merely takes one or a plurality of gel packs that have been frozen with him or her and places them as previously described and actuates the device so as to provide cooling air for up to two hours or until the gel pack no longer is capable of delivering a cooling effect.

Various changes and modifications will suggest themselves to those skilled in the art and all such changes and modifications are intended to be covered by the appended claims.

While the present invention has been described with regards to particular embodiments, it is recognized that other variations of the present invention may be devised without departing from the disclosed inventive concept.

What is claimed is:

1. A personal cooling device comprising the combination of:
   a tapered body member forming an open topped housing containing a switch actuated, motor operated fan adapted to be battery energized and having a platform positioned over said fan and adapted to receive a coolant member thereon and a cap member adapted to receive said coolant member releasably secured to said open topped housing for ease of access into said housing.

2. The personal cooling device in accordance with claim 1, wherein the side walls of said body member are apertured to permit ambient air being drawn into said housing.

3. The personal cooling device in accordance with claim 2, wherein said cap member is apertured to allow the passage of air from the interior of said housing upward and outward therefrom.

4. The personal cooling device in accordance with claim 3, wherein said platform is apertured to allow the passage of air therethrough and said body member has opposed tether retaining means whereby a tether may be secured thereto for placing said personal cooling device around the neck of a user thereof.

5. The personal cooling device in accordance with claim 4, wherein said cooling device has a clip member whereby same may be clipped onto the waistband of a garment worn by the user thereof.

6. The personal cooling device in accordance with claim 5, wherein said body member and said cap member are of molded plastic.

7. The personal cooling device in accordance with claim 6, wherein said coolant comprises a gel pack congruently configured to fit within said housing member on said apertured platform.

8. The personal cooling device in accordance with claim 7, wherein said personal cooling device is conically shaped and the terminus thereof is a switch for actuating said motor operated fan.

9. A personal cooling device comprising the combination of:

- a body member having an upper wide-mouth portion forming a recess and a lower conically shaped portion, said upper wide-mouth portion having a retaining means within said recess and being adapted to retain a coolant member in releasable fashion thereon;
- a fan blade operatively disposed within said recess and below said retaining means, said housing contiguous to said fan blade having spaced apertures communicating to the ambient atmosphere; and
- said lower conically shaped portion housing a motor operatively connected to said fan blade and being adapted to receive batteries in energizing relationship to said motor, switch and circuitry means for energizing said motor and a cap member releasably associated with said wide-mouth portion of said body member, said cap member adapted to retain said coolant member in releasable fashion therein.

* * * * *